(12) United States Patent
Treado et al.

(10) Patent No.: US 9,052,290 B2
(45) Date of Patent: *Jun. 9, 2015

(54) SWIR TARGETED AGILE RAMAN SYSTEM FOR DETECTION OF UNKNOWN MATERIALS USING DUAL POLARIZATION

(71) Applicant: Chemimage Corporation, Pittsburgh, PA (US)

(72) Inventors: Patrick J. Treado, Pittsburgh, PA (US); Matthew Nelson, Harrison City, PA (US); Charles Gardner, Gibsonia, PA (US)

(73) Assignee: ChemImage Corporation, Pittsburgh, PA (US)

( * ) Notice: Subject to any disclaimer, the term of this patent is extended or adjusted under 35 U.S.C. 154(b) by 86 days.

This patent is subject to a terminal disclaimer.

(21) Appl. No.: 13/842,034

(22) Filed: Mar. 15, 2013

(65) Prior Publication Data

US 2014/0104607 A1    Apr. 17, 2014

Related U.S. Application Data (63) Continuation-in-part of application No. 13/729,220, filed on Dec. 28, 2012, and a continuation-in-part of application No. 13/729,171, filed on Dec. 28, 2012, and a continuation-in-part of application No. 13/651,600, filed on Oct. 15, 2012.

(51) Int. Cl.
*G01J 3/44* (2006.01)
*G01N 21/65* (2006.01)
(Continued)

(52) U.S. Cl.
CPC . *G01N 21/65* (2013.01); *G01J 3/02* (2013.01); *G01J 3/0264* (2013.01); *G01J 3/2823* (2013.01);
(Continued)

(58) Field of Classification Search
CPC .......... G01J 3/44; G01J 3/0224; G01N 21/35; G01N 21/359; G01N 21/21
USPC .......... 356/72–73, 301, 369; 250/341.3, 338.1
See application file for complete search history.

(56) References Cited

U.S. PATENT DOCUMENTS

| 4,560,275 A | 12/1985 | Goetz |
| 4,749,257 A | 6/1988 | Klausz |

(Continued)

FOREIGN PATENT DOCUMENTS

| EP | 2083259 | 7/2009 |
| WO | WO/91/08466 | 6/1991 |

(Continued)

OTHER PUBLICATIONS

Sharma. et al. "Stand-Off Raman Spectroscopic Detection of Minerals on Planetary Surfaces", Hawaii Institute of Geophysics and Planetology, pp. 2391-2407, 2003.

(Continued)

*Primary Examiner* — Kara E Geisel
(74) *Attorney, Agent, or Firm* — Pepper Hamilton LLP (57) ABSTRACT

The present disclosure provides for a system and method for analyzing a sample comprising at least one unknown material. A first location may be scanned to generate a SWIR hyperspectral image. The SWIR hyperspectral image may be generated using dual polarization techniques. The SWIR hyperspectral image may be analyzed to target a second location comprising the unknown material. This second location may be further analyzed using Raman spectroscopic techniques and a Raman data set may be generated. The Raman data set may be further analyzed to associate the unknown material with a know material.

22 Claims, 9 Drawing Sheets

(51) Int. Cl.
  *G01J 3/02*   (2006.01)
  *G01J 3/28*   (2006.01)
  *G01J 3/36*   (2006.01)
  *G01N 33/22*  (2006.01)
  *G01N 21/17*  (2006.01)

(52) U.S. Cl.
  CPC .... *G01J 3/36* (2013.01); *G01J 3/44* (2013.01); *G01N 33/22* (2013.01); *G01N 2021/1738* (2013.01); *G01N 2021/174* (2013.01); *G01N 2021/1744* (2013.01); *G01J 3/0221* (2013.01); *G01N 2201/0833* (2013.01); *G01N 2201/0846* (2013.01)

(56) References Cited

U.S. PATENT DOCUMENTS

| | | | |
|---|---|---|---|
| 5,080,486 | A | 1/1992 | Shirasaki |
| 5,097,352 | A | 3/1992 | Takahashi |
| 5,196,682 | A | 3/1993 | Englehardt |
| 5,216,484 | A | 6/1993 | Chao et al. |
| 5,321,539 | A | 6/1994 | Hirabayashi |
| 5,394,237 | A | 2/1995 | Chang |
| 5,657,121 | A | 8/1997 | Nishina |
| 5,740,288 | A | 4/1998 | Pan |
| 6,002,476 | A | 12/1999 | Treado |
| 6,006,140 | A | 12/1999 | Carter |
| 6,014,475 | A | 1/2000 | Frisken |
| 6,244,535 | B1 | 6/2001 | Felix |
| 6,262,851 | B1 | 7/2001 | Marshall |
| 6,274,871 | B1 | 8/2001 | Dukor et al. |
| 6,415,077 | B1 | 7/2002 | Frisken |
| 6,422,508 | B1 | 7/2002 | Barnes |
| 6,477,907 | B1 | 11/2002 | Chambers |
| 6,522,467 | B1 | 2/2003 | Li |
| 6,606,566 | B1 | 8/2003 | Sunshine |
| 6,658,915 | B2 | 12/2003 | Sunshibne |
| 6,717,668 | B2 | 4/2004 | Treado |
| 6,820,012 | B2 | 11/2004 | Sunshine |
| 6,844,817 | B2 | 1/2005 | Gleine |
| 6,967,612 | B1 | 11/2005 | Gorman |
| 6,985,216 | B2 | 1/2006 | Treado |
| 6,985,233 | B2 | 1/2006 | Tuschel |
| 7,012,695 | B2 | 3/2006 | Maier |
| 7,084,972 | B2 | 8/2006 | Treado |
| 7,088,435 | B2 | 8/2006 | Brestel et al. |
| 7,164,117 | B2 | 1/2007 | Breed |
| 7,239,974 | B2 | 7/2007 | Gulati |
| 7,246,613 | B1 | 7/2007 | Mohar |
| 7,262,839 | B2 | 8/2007 | Treado |
| 7,277,178 | B2 | 10/2007 | Shpantzer |
| 7,286,222 | B2 | 10/2007 | Gardner |
| 7,295,308 | B1 | 11/2007 | Samuels |
| 7,307,705 | B2 | 12/2007 | Treado |
| 7,322,267 | B1 | 1/2008 | Munson |
| 7,386,372 | B2 | 6/2008 | Breed |
| 7,417,727 | B2 | 8/2008 | Polonskiy |
| 7,420,664 | B2 | 9/2008 | Treado et al. |
| 7,420,675 | B2 | 9/2008 | Giakos |
| 7,440,096 | B2 | 10/2008 | Gardner |
| 7,460,227 | B1 | 12/2008 | Kim |
| 7,486,395 | B2 | 2/2009 | Treado |
| 7,502,118 | B2 | 3/2009 | Shpantzer |
| 7,511,624 | B2 | 3/2009 | Shaw |
| 7,525,102 | B1 | 4/2009 | Henshaw |
| 7,542,138 | B2 | 6/2009 | Gardner |
| 7,548,310 | B2 | 6/2009 | Gardner |
| 7,551,715 | B2 | 6/2009 | Rothschild |
| 7,573,570 | B2 | 8/2009 | Zhang |
| 7,596,242 | B2 | 9/2009 | Breed |
| 7,644,606 | B2 | 1/2010 | Sheen |
| 7,663,502 | B2 | 2/2010 | Breed |
| 7,676,062 | B2 | 3/2010 | Breed |
| 7,687,276 | B2 | 3/2010 | Kunz |
| 7,692,775 | B2 | 4/2010 | Treado et al. |
| 8,379,193 | B2 | 2/2013 | Gardner |
| 2001/0052979 | A1 | 12/2001 | Treado et al. |
| 2003/0058112 | A1 | 3/2003 | Gleine |
| 2003/0108284 | A1 | 6/2003 | Danagher |
| 2003/0123056 | A1 | 7/2003 | Barnes |
| 2003/0216869 | A1 | 11/2003 | Sunshine |
| 2004/0051867 | A1 | 3/2004 | Brestel |
| 2004/0109232 | A1 | 6/2004 | Riza |
| 2004/0191859 | A1 | 9/2004 | Tabacco |
| 2005/0015004 | A1 | 1/2005 | Hertel |
| 2005/0030533 | A1 | 2/2005 | Treado |
| 2005/0030545 | A1 | 2/2005 | Tuschel |
| 2005/0030657 | A1 | 2/2005 | Maier |
| 2005/0041244 | A1 | 2/2005 | Treado |
| 2005/0079626 | A1 | 4/2005 | Kunz |
| 2005/0105099 | A1 | 5/2005 | Shpantzer |
| 2005/0148842 | A1 | 7/2005 | Wang |
| 2005/0228452 | A1 | 10/2005 | Mourlas |
| 2005/0264813 | A1 | 12/2005 | Giakos |
| 2006/0007437 | A1 | 1/2006 | Treado |
| 2006/0021498 | A1 | 2/2006 | Moroz |
| 2006/0119797 | A1 | 6/2006 | Ockenfuss |
| 2006/0146315 | A1 | 7/2006 | Treado |
| 2006/0167595 | A1 | 7/2006 | Breed |
| 2006/0170922 | A1 | 8/2006 | Wang et al. |
| 2006/0203238 | A1 | 9/2006 | Gardner |
| 2006/0208169 | A1 | 9/2006 | Breed |
| 2006/0209301 | A1 | 9/2006 | Gardner |
| 2006/0254522 | A1 | 11/2006 | Shaw |
| 2006/0256330 | A1 | 11/2006 | Leipertz |
| 2006/0262304 | A1 | 11/2006 | Carron |
| 2006/0268266 | A1 | 11/2006 | Gardner |
| 2007/0007384 | A1 | 1/2007 | Sliwa |
| 2007/0081156 | A1 | 4/2007 | Treado |
| 2007/0086624 | A1 | 4/2007 | Breed |
| 2007/0098142 | A1 | 5/2007 | Rothschild |
| 2007/0118324 | A1 | 5/2007 | Gulati |
| 2007/0125951 | A1 | 6/2007 | Snider |
| 2007/0127030 | A1 | 6/2007 | Shpantzer |
| 2007/0153268 | A1 | 7/2007 | Panza et al. |
| 2007/0163431 | A1 | 7/2007 | Mohar |
| 2007/0216898 | A1 | 9/2007 | Gardner |
| 2007/0262574 | A1 | 11/2007 | Breed |
| 2007/0268485 | A1 | 11/2007 | Polonskiy |
| 2007/0282506 | A1 | 12/2007 | Breed |
| 2008/0036580 | A1 | 2/2008 | Breed |
| 2008/0036593 | A1 | 2/2008 | Rose-Pehrsson |
| 2008/0051957 | A1 | 2/2008 | Breed |
| 2008/0084560 | A1 | 4/2008 | Zhang |
| 2008/0088837 | A1 | 4/2008 | Gardner |
| 2008/0129581 | A1 | 6/2008 | Douglass |
| 2008/0144885 | A1 | 6/2008 | Zucherman |
| 2008/0154535 | A1 | 6/2008 | Sparks |
| 2008/0157940 | A1 | 7/2008 | Breed |
| 2008/0165344 | A1 | 7/2008 | Treado |
| 2008/0180675 | A1 | 7/2008 | Sheen |
| 2008/0191137 | A1 | 8/2008 | Poteet |
| 2008/0198365 | A1 | 8/2008 | Treado |
| 2008/0204757 | A1 | 8/2008 | Manning |
| 2008/0212180 | A1 | 9/2008 | Zhang |
| 2008/0236275 | A1 | 10/2008 | Breed |
| 2008/0258071 | A1 | 10/2008 | Arnold |
| 2008/0268548 | A1 | 10/2008 | Zuckerman |
| 2008/0295783 | A1 | 12/2008 | Furton |
| 2009/0046538 | A1 | 2/2009 | Breed |
| 2009/0092284 | A1 | 4/2009 | Breed |
| 2009/0095885 | A1 | 4/2009 | Hager |
| 2009/0101843 | A1 | 4/2009 | Henshaw |
| 2009/0128802 | A1 | 5/2009 | Treado et al. |
| 2009/0202128 | A1 | 8/2009 | Gorian et al. |
| 2009/0236528 | A1 | 9/2009 | Shpantzer |
| 2009/0252650 | A1 | 10/2009 | Lakshmanan |
| 2009/0257555 | A1 | 10/2009 | Chalmers |
| 2010/0225899 | A1 | 9/2010 | Treado |

FOREIGN PATENT DOCUMENTS

| | | |
|---|---|---|
| WO | WO/01/33212 | 5/2001 |
| WO | WO/03/059735 | 7/2003 |

(56) References Cited

FOREIGN PATENT DOCUMENTS

| WO | WO/03/102534 | 11/2003 |
|---|---|---|
| WO | WO/2005/008198 | 1/2005 |
| WO | WO/2005008200 | 1/2005 |
| WO | WO/2005/010474 | 3/2005 |
| WO | WO2006058306 | 6/2006 |
| WO | WO/2007/001379 | 1/2007 |
| WO | WO/2007/011391 | 1/2007 |
| WO | WO/2007/013000 | 2/2007 |
| WO | WO/2007/032814 | 3/2007 |
| WO | WO/2007/044067 | 4/2007 |
| WO | WO/2007/044593 | 4/2007 |
| WO | WO/2007/051092 | 5/2007 |
| WO | WO/2007/056753 | 5/2007 |
| WO | WO/2007/084099 | 7/2007 |
| WO | WO/2007/101297 | 9/2007 |
| WO | WO/2007/120996 | 10/2007 |
| WO | WO/2007/103897 | 11/2007 |
| WO | WO/2007/123555 | 11/2007 |
| WO | WO/2008/002659 | 1/2008 |
| WO | WO/2008/010832 | 1/2008 |
| WO | WO/2008/048979 | 4/2008 |
| WO | WO/2008/024344 | 6/2008 |
| WO | WO/2008/097262 | 8/2008 |
| WO | WO/2008/105812 | 9/2008 |
| WO | WO2008108846 | 9/2008 |
| WO | WO/2008/140473 | 11/2008 |

OTHER PUBLICATIONS

Sharma, et al, Portable Stand-off Raman and Mie-Rayleigh LIDAR for Cloud, Aerosols, and Chemical Monitoring. Proceedings of SPIE vol. 5154, LIDAR Remote Sensing for Environmental Monitoring IV, pp. 1-14, 2003.

Sharma, et al., Remote Pulsed Laser Raman Spectroscopy System for Mineral Analysis on Planetary Surfaces to 66 Meters, Applied Spectroscopy, vol. 56, No. 6, 2002, pp. 699-705.

PCT/US06/2647, Notification of Transmittal of the International Search Report and the Written Opinion of the International Searching Authority, Mar. 31, 2008.

Gardner, C. et al, "Remote Chemical Biological and Explosive Agent Detection Using a Robot-Based Raman Detector", SPIE Defense + Security, Proc. SPIE 6962, 69620T (2008).

Pati, B. et al., "Passively Q-switched Nd:YLF laser in a D-rod configuration," in Conference on Lasers and Electro-Optics, OSA Technical Digest (Optical Society of America, Washington, DC 2008), paper CF J5.

Fuller, M. et al., "High gain end pumped lasers," OSA TOPS, vol. 19, Advanced Solid State Lasers, Walter Bosenberg and Martin M. Feijer (eds), 1998, Optical Society of America.

Kyusho, Y et al., "High-energy subnanosecond compact laser system with diode-pumped, Q-switched Nd: YVO4 laser," OSA TOPS on Advanced Solid State Lasers, vol. 1, Stephen A. Payne and Clifford Pollock (eds), 1996, Optical Society of America.

Zheng, S. et al, "Laser-diode end-pumped passively Q-switched laser with Cr4+:YAG saturable absorber," Opt. Engineering, vol. 41, # 9, 2002, pp. 2271-2275.

Nelson et al, "Single-Shot Multiwavelength Imaging of Laser Plumes," Applied Spectroscopy, vol. 52, No. 2, Feb. 1, 1998.

Extended European Search Report, PCT/US2006022647, Aug. 10, 2010.

Kline, Nicole J. et al., Raman Chemical Imaging of Breast Tissue, Journal of Raman Spectroscopy, vol. 28, 119-124 (1997).

Levenson, Richard, "Spectral Imaging and Pathology: Seeing More," Laboratory Medicine, Apr. 2004, vol. 35, pp. 244-251.

Levenson, Richard et al, "Multiplexing with multispectral Imaging: from Mice to Microscopy," available from: http://www.cri-inc.com/assets/nuance/MultiplexingwithMSlfrommicetomicroscopy.pdf, last accessed Nov. 23, 2010.

SWIR TARGETED AGILE RAMAN SYSTEM FOR DETECTION OF UNKNOWN MATERIALS USING DUAL POLARIZATION

RELATED APPLICATIONS

This application is a continuation-in-part to pending U.S. patent application Ser. No. 13/729,220, filed on Dec. 28, 2012, entitled "Targeted Agile Raman System for Detection of Unknown Materials," and pending U.S. patent application Ser. No. 13/729,171, filed on Dec. 28, 2012, also entitled "Targeted Agile Raman System for Detection of Unknown Materials." This application is also a continuation-in-part to pending U.S. patent application Ser. No. 13/651,600, filed on Oct. 15, 2012, entitled "Dual Polarization with Liquid Crystal Tunable Filters." These applications are hereby incorporated by reference in their entireties.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the an entire area encompassing the sample simultaneously using an electronically tunable optical imaging filter such as an acousto-optic tunable filter (AOTF) or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image.

Spectroscopic devices operate over a range of wavelengths due to the operation ranges of the detectors or tunable filters possible. This enables analysis in the Ultraviolet (UV), visible (VIS), near infrared (NIR), short-wave infrared (SWIR), mid infrared (MIR) wavelengths and to some overlapping ranges. These correspond to wavelengths of about 180-380 nm (UV), about 380-700 nm (VIS), about 700-2500 nm (NIR), about 900-1700 nm (SWIR), and about 2500-25000 nm (MIR).

There exists a need for accurate and reliable detection of unknown materials at standoff distances. Additionally, it would be advantageous if a standoff system and method could be configured to operate in an On-the-Move (OTM) mode. It would also be advantageous if a system and method could be configured for deployment on a small unmanned ground vehicle (UGV).

A LCTF uses birefringent retarders to distribute the light energy of an input light signal over a range of polarization states. The polarization state of light emerging at the output of the LCTF is caused to vary as a function of wavelength due to differential retardation of orthogonal components of the light, contributed by the birefringent retarders. The LCTF discriminates for wavelength-specific polarization using a polarizing filter at the output. The polarizing filter passes the light components in the output that are rotationally aligned to the polarizing filter. The LCTF is tuned by adjusting the birefringence of the retarders so that a specific discrimination wavelength emerges in a plane polarized state, aligned to the output polarizing filter. Other wavelengths that emerge in other polarization states and/or alignments are attenuated.

A highly discriminating spectral filter is possible using a sequence of several birefringent retarders. The thicknesses, birefringences, and relative rotation angles of the retarders are chosen to correspond to the discrimination wavelength. More specifically, the input light signal to the filter becomes separated into orthogonal vector components, parallel to the respective ordinary and extraordinary axes of each birefringent retarder when encountered along the light transmission path through the filter. These separated vector components are differentially retarded due to the birefringence; such differential retardation also amounts to a change in their polarization state. For a plane polarized component at the input to the filter, having a specific rotational alignment at the input to the filter and at specific discrimination wavelengths, the light components that have been divided and subdivided all emerge from the filter in the same polarization state and alignment, namely plane polarized and in alignment with the selection polarizer (i.e., the polarizing filter) at the output.

A filter as described is sometimes termed an interference filter because the components that have been divided and subdivided from the input and interfere positively at the output selection polarizer are the components that are passed. Such filters also are sometimes described with respect to a rotational twist in the plane polarization alignment of the discriminated component between the input and the selection polarizer at the output.

There are several known configurations of spectral filters comprising birefringent retarders, such as the Lyot, Solc and Evans types. Such filters can be constructed with fixed (non-tunable) birefringent crystals for the retarders. A filter with retarders that are tuned in unison permits adjustment of the bandpass wavelength. Tunable retarders can comprise liquid crystals or composite retarder elements each comprising a fixed crystal and an optically aligned liquid crystal.

The thicknesses, birefringences, and rotation angles of the retarders are coordinated such that each retarder contributes part of the necessary change in polarization state to alter the polarization state of the passband wavelength from an input reference angle to an output reference angle. The input reference angle may be, for example, 45° to the ordinary and extraordinary axes of a first retarder in the filter. The output reference angle is the rotational alignment of the polarizing filter (or "selection polarizer").

A spectral filter may have a comb-shaped transmission characteristic. Increasing or decreasing the birefringence when tuning to select the discrimination wavelength (or passband), stretches or compresses the comb shape of the transmission characteristic along the wavelength coordinate axis.

If the input light is randomly polarized, the portion that is spectrally filtered is limited to the vector components of the input wavelengths that are parallel to one of the two orthogonal polarization components that are present. Only light at the specific wavelength, and at a given reference polarization alignment at the input, can emerge with a polarization angle aligned to the rotational alignment of the selection polarizer at the output. The light energy that is orthogonal to the reference alignment at the input, including light at the passband wavelength, is substantially blocked.

A LCTF thus passes only one of two orthogonal components of input light. The transmission ratio in the passband is at a maximum for incident light at the input to the LCTF that is aligned to a reference angle of the LCTF. Transmission is at minimum for incident light energy at the input is orthogonal to that reference angle. If the input light in the passband is randomly polarized, the best possible transmission ratio in the passband is fifty percent. It is therefore desirable to devise a system and method wherein both orthogonal components of the input light are allowed to transmit through the tunable filter, thereby effectively doubling the throughput at the filter output.

SUMMARY

The present invention relates generally to a system and method for detecting unknown materials in a sample scene. More specifically, the present disclosure relates to scanning sample scenes using SWIR hyperspectral imaging and then interrogating areas of interest using Raman spectroscopy. One term that may be used to describe the system and method of the present disclosure is Agile Laser Scanning ("ALS") Raman spectroscopy. The term is used to describe the ability to focus the area of interrogation by Raman spectroscopy to those areas defined by hyperspectral imaging with high probabilities of comprising unknown materials. Examples of materials that may be assessed using the system and method of the present disclosure may include, but are not limited to, chemical, biological, and explosive threat agents as well as other hazardous materials, contaminants, and drugs (both legal and illicit).

The present disclosure provides for hyperspectral imaging using techniques for dual beam processing through a plurality of tunable filters, including processing both orthogonal polarization components of the incident light at the input to the tunable filter. The configuration provided herein overcomes the limitations of the prior art by maximizing the light transmission ratio during spectrally filtered imaging using the tunable filter.

The present disclosure relates to a method for spectral imaging using two tunable filters sensitive to a polarization orientation of a light input beam from an objective lens, wherein the light input beam is to be spectrally filtered by the two tunable filters and coupled to at least one imaging lens. The method comprises: splitting the light input beam into a first and a second beams with respectively orthogonal polarization components; applying the first beam to a first one of the two tunable filters and the second beam to a second one of the two tunable filters such that a polarization component in each of the first and the second beams is filtered by a respective tunable filter to transmit a corresponding passband wavelength; and arranging the imaging lens relative to filtered first and second beams at respective outputs of the two tunable filters so as to focus images from both of the filtered first and second beams. The present disclosure contemplates that the filtered beams may be displayed in either an overlaid or non-overlaid configuration. The present disclosure also contemplates that the beams may be displayed on a single detector or more than one detector.

It is an aspect of the disclosure that these techniques can be accomplished in a way that facilitates use of the tunable filter in imaging applications. In that case, the two tunable filters can be oriented orthogonally relative to one another, and disposed to form an image through the same optics. The input light is split into its orthogonal plane polarized beams and each beam is aligned to the reference angle of one of the tunable filters. The resulting cross-polarized images are either overlaid on one another or displayed in a non-overlaid configuration.

In this embodiment, it is possible to tune the two adjacent tunable filters to the same passband, thereby maximizing the intensity of the passband at the photodetector array. Alternatively, the two adjacent tunable filters can be tuned to different passband wavelengths. In a case where a given material or object of interest is characterized by two wavelength peaks, simultaneously displaying the images at two distinct wavelengths on one or more detectors holds potential for increasing the speed of detection. For example, if two images are displayed simultaneously for a material or object characterized by two wavelength peaks, then the speed of detection becomes the frame rate of the camera. Such a configuration holds potential for detection in real time. In other embodiments where a material or object is characterized by n-number of wavelength peaks, then detection can be achieved in a shorter amount of time (for example, detection in half the time).

Alternative embodiments wherein the images are overlaid on each other holds potential or substantially increasing the contrast for that species in the composite image, even in the presence of other species that might be detectable at one but not both of the same wavelengths.

According to an aspect of this disclosure, an imaging system is provided with at least one imaging lens or lens assembly and a plurality of spectral filters that rely on polarization alignment. In particular, the spectral filter(s) can comprise one or more tunable filters. The optics can be infinitely corrected or the tunable filter can be disposed at a focal plane. The objective lens collects light from a sample, for example laser-excited Raman radiation, and directs the light, for example as a collimated beam, to a tunable filter. Such a filter is inherently sensitive to polarization state. Light emerging from the spectral filter is coupled through the imaging lens to be resolved on an image plane such as a CCD photosensor array.

As discussed above, in a conventional tunable filter configuration, the output beam (i.e., the filtered output from the tunable filter) is limited to one of two orthogonal polarization components of the collected light, which in the case of random polarization is 50% of the light power. However, the configurations of the present disclosure hold potential for increasing the intensity of the image at a photodetector array.

One polarization component of the light from the sample can be transmitted directly through a polarization beam splitter. This component is plane polarized and incident on the tunable filter at the reference alignment of the tunable filter. Therefore, this component is provided at the polarization alignment that obtains a maximum transmission ratio of the passband through the tunable filter.

An alternative embodiment has two orthogonally aligned beam paths and two orthogonally aligned tunable filters. The input light is split into orthogonal beams as above. The two tunable filters are placed along laterally adjacent beam paths. One of the beam paths and tunable filters can operate as already described. The tunable filter on the second beam path can be tuned to the same or a different wavelength. The tunable filter on the second beam path can be oriented parallel to the first tunable filter and preceded by a half wave plate at 45° so as to pre-orient the second beam. Or in another alternative, the half wave plate is omitted and the second tunable filter is physically rotated ±90° from parallel to the first tunable filter. When the tunable filters are tuned to the same wavelengths, the overlaid images are cross-polarized and image intensity at the detector is at the maximum. When the tunable filters are tuned to different wavelengths, the image intensities are at half maximum. However, the dual polarization configuration of the present disclosure holds potential for enhancing the contrast in a resulting image.

Hyperspectral imaging may be implemented to define areas where the probability of finding unknown materials is high. The advantage of using hyperspectral imaging in a scanning mode is its speed of analysis. Raman spectroscopy provides for chemical specificity and may therefore be implemented to interrogate those areas of interest identified by the hyperspectral image. The present disclosure provides for a system and method that combines these two techniques, using the strengths of each, to provide for a novel technique of achieving rapid, reliable, and accurate evaluation of unknown materials. The system and method also hold potential for providing autonomous operation as well as providing considerable flexibility for an operator to tailor searching for specific applications.

The present disclosure contemplates both static and On-the-Move ("OTM") standoff configurations. The present disclosure also contemplates the implementation of the sensor system of the present disclosure onto an Unmanned Ground Vehicle ("UGV"). Integration of these sensors onto small UGV platforms in conjunction with specific laser systems may be configured to achieve a pulsed laser system with a size, weight, and power consumption compatible with small UGV operation. Such a configuration holds potential for implementation in a laser-based OTM explosive location system on a small UGV.

The present disclosure also provides for the application of various algorithms to provide for data analysis and object imaging and tracking. These algorithms may further comprise image-based material detection algorithms, including tools that may determine the size, in addition to identity and location, of unknown materials. Providing this information to an operator may hold potential for determining the magnitude of unknown materials in a wide area surveillance mode. Additionally, algorithms may be applied to provide for sensor fusion. This fusion of Raman and other spectroscopic and/or imaging modalities holds potential for reducing false alarm rates.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

DETAILED DESCRIPTION

Reference will now be made in detail to the embodiments of the present disclosure, examples of which are illustrated in the accompanying drawings. Wherever possible, the same reference numbers will be used throughout the drawings to refer to the same or like parts.

Figure 1:
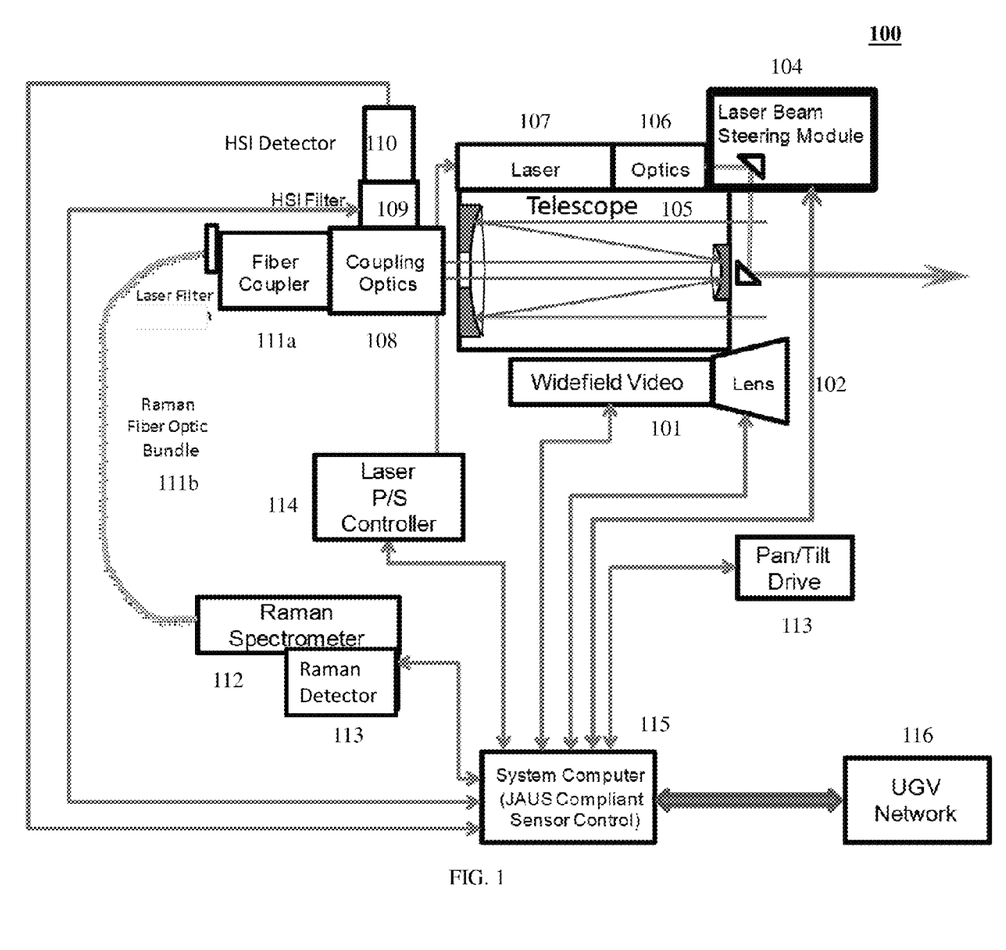
FIG. 1 is a schematic representation of a system of the present disclosure.

The present disclosure provides for a system combining SWIR hyperspectral imaging and Raman spectroscopic techniques, one embodiment of which is illustrated in FIG. 1. The system 100 may comprise a widefield video capture device 101 which may be used to scan sample scenes. The video capture device 101 may be coupled to a lens 102. A telescope optic 105 may be used to focus light on various sample locations and/or collect interacted photons from these locations.

When scanning a first location, the system 100 may collect interacted photons and pass them through a coupling optic 108. The coupling optic 108 may comprise a beamsplitter, or other element, to direct interacted photons to either the filter 109 or the fiber coupler 111a. In a scanning modality, the interacted photons are directed to the filter 109. In the embodiment of FIG. 1, the filter 109 is illustrated as comprising a tunable filter. The tunable filter may filter the interacted photons into a plurality of wavelength bands and these filtered photons may be detected by a detector 110. The present disclosure contemplates a variety of different hyperspectral imaging modalities may be used to scan the first location. Therefore, the detector 110 may comprise at least one of: an InGaAs detector, a CCD detector, a CMOS detector, an InSb detector, a MCT detector, and combinations thereof. The detector 110 may be configured to generate a test data set representative of the first location.

When assessing a second location, a laser illumination source 107 may illuminate the second location to generate a second plurality of interacted photons. The system 100 may further comprise optics 106, and laser beam steering module 104. In one embodiment, the laser light source 107 may comprise a Nd:YLF laser. The interacted photons may be collected using the telescope optics 105 and pass through the coupling optic 108. In this interrogation mode, the coupling optic 108 may direct interacted photons to a fiber coupler 111a and to a FAST device 111b.

A FAST device, when used in conjunction with a photon detector, allows massively parallel acquisition of full-spectral images. A FAST device can provide rapid real-time analysis for quick detection, classification, identification, and visualization of the sample. The FAST technology can acquire a few to thousands of full spectral range, spatially resolved spectra simultaneously. A typical FAST array contains multiple optical fibers that may be arranged in a two-dimensional array on one end and a one dimensional (i.e., linear) array on the other end. The linear array is useful for interfacing with a photon detector, such as a charge-coupled device ("CCD"). The two-dimensional array end of the FAST is typically positioned to receive photons from a sample. The photons from the sample may be, for example, emitted by the sample, absorbed by the sample, reflected off of the sample, refracted by the sample, fluoresce from the sample, or scattered by the sample. The scattered photons may be Raman photons.

In a FAST spectrographic system, photons incident to the two-dimensional end of the FAST may be focused so that a spectroscopic image of the sample is conveyed onto the two-dimensional array of optical fibers. The two-dimensional array of optical fibers may be drawn into a one-dimensional distal array with, for example, serpentine ordering. The one-dimensional fiber stack may be operatively coupled to an imaging spectrometer of a photon detector, such as a charge-coupled device so as to apply the photons received at the two-dimensional end of the FAST to the detector rows of the photon detector.

One advantage of this type of apparatus over other spectroscopic apparatus is speed of analysis. A complete spectroscopic imaging data set can be acquired in the amount of time it takes to generate a single spectrum from a given material. Additionally, the FAST can be implemented with multiple detectors. A FAST system may be used in a variety of situations to help resolve difficult spectrographic problems such as the presence of polymorphs of a compound, sometimes referred to as spectral unmixing.

FAST technology can be applied to the collection of spatially resolved Raman spectra. In a standard Raman spectroscopic sensor, a laser beam is directed on to a sample area, an appropriate lens is used to collect the Raman scattered light, the light is passed through a filter to remove light scattered at the laser wavelength and finally sent to the input of a spectrometer where the light is separated into its component wavelengths dispersed at the focal plane of a CCD camera for detection. In the FAST approach, the Raman scattered light, after removal of the laser light, is focused onto the input of a fiber optic bundle consisting of up to hundreds of individual fiber, each fiber collecting the light scattered by a specific location in the excited area of the sample. The output end of each of the individual fibers is aligned at the input slit of a spectrometer that is designed to give a separate dispersive spectrum from each fiber. A 2-dimensional CCD detector is used to capture each of these FAST spectra. As a result, multiple Raman spectra and therefore, multiple interrogations of the sample area can be obtained in a single measurement cycle, in essentially the same time as in conventional Raman sensors.

In one embodiment, an area of interest can be optically matched by the FAST array to the area of the laser spot to maximize the collection Raman efficiency. In one embodiment, the present disclosure contemplates another configuration in which only the laser beam be moved for scanning within a FOV. It is possible to optically match the scanning FOV with the Raman collection FOV. The FOV is imaged onto a rectangular FAST array so that each FAST fiber is collecting light from one region of the FOV. The area per fiber which yields the maximum spatial resolution is easily calculated by dividing the area of the entire FOV by the number of fibers. Raman scattering is only generated when the laser excites a sample, so Raman spectra will only be obtained at those fibers whose collection area is being scanned by the laser beam. Scanning only the laser beam is a rapid process that may utilize by off-the-shelf galvanometer-driven mirror systems.

The system 100 may also comprise a pan/tilt unit 103 for controlling the position of the system, a laser P/S controller 114 for controlling the laser, and a system computer 115 for controlling the elements of the system. The system may also comprise an operator control unit 116 although this is not necessary. The operator control unit 116 may comprise the user controls for the system and may be a terminal, a lap top, a keyboard, a display screen, and the like.

In one embodiment, the system of the present disclosure is configured to operate in a pulsed laser excitation/time-gated detection configuration. This may be enabled by utilizing an ICCD detector. However, the present disclosure also contemplates the system may be configured in a continuous mode using at least one of: a continuous laser, a shutter, and a continuous camera.

In one embodiment of the present disclosure, the SWIR portion of the system may comprise an InGaAs focal plane camera coupled to a wavelength-agile tunable filter and an appropriate focusing lens. Components may be selected to allow images generated by light reflecting off a target are to be collected over the 900 to 1700 nm wavelength region. This spectral region may be chosen because most explosives of interest exhibit molecular absorption in this region. Additionally, solar radiation (i.e., the sun) or a halogen lamp may be used as the light source in a reflected light measurement. The system may be configured to stare at a FOV or target area determined by the characteristics of the lens, and the tunable filter may be used to allow light at a single wavelength to reach the camera. By changing the wavelength of the tunable filter, the camera can take multiple images of the light reflected from a target area at wavelengths characteristic of various explosives and of background. These images can be rapidly processed to create chemical images, including hyperspectral images. In such images, the contrast is due to the presence or absence of a particular chemical or explosive material. The strength of SWIR hyperspectral imaging for OTM is that it is fast. Chemical images can be acquired, processed, and displayed quickly, in some instances in the order of tens of milliseconds.

The present disclosure also contemplates an embodiment wherein the system is attached to a vehicle and operated via unbilical while the UGV is moved (full interrogation of the system on a UGV). In another embodiment, the system described herein may be configured to operate via robotics. A small number of mounting brackets and plates may be fabricated in order to carry out the mounting sensor on the UGV.

Figure 2:
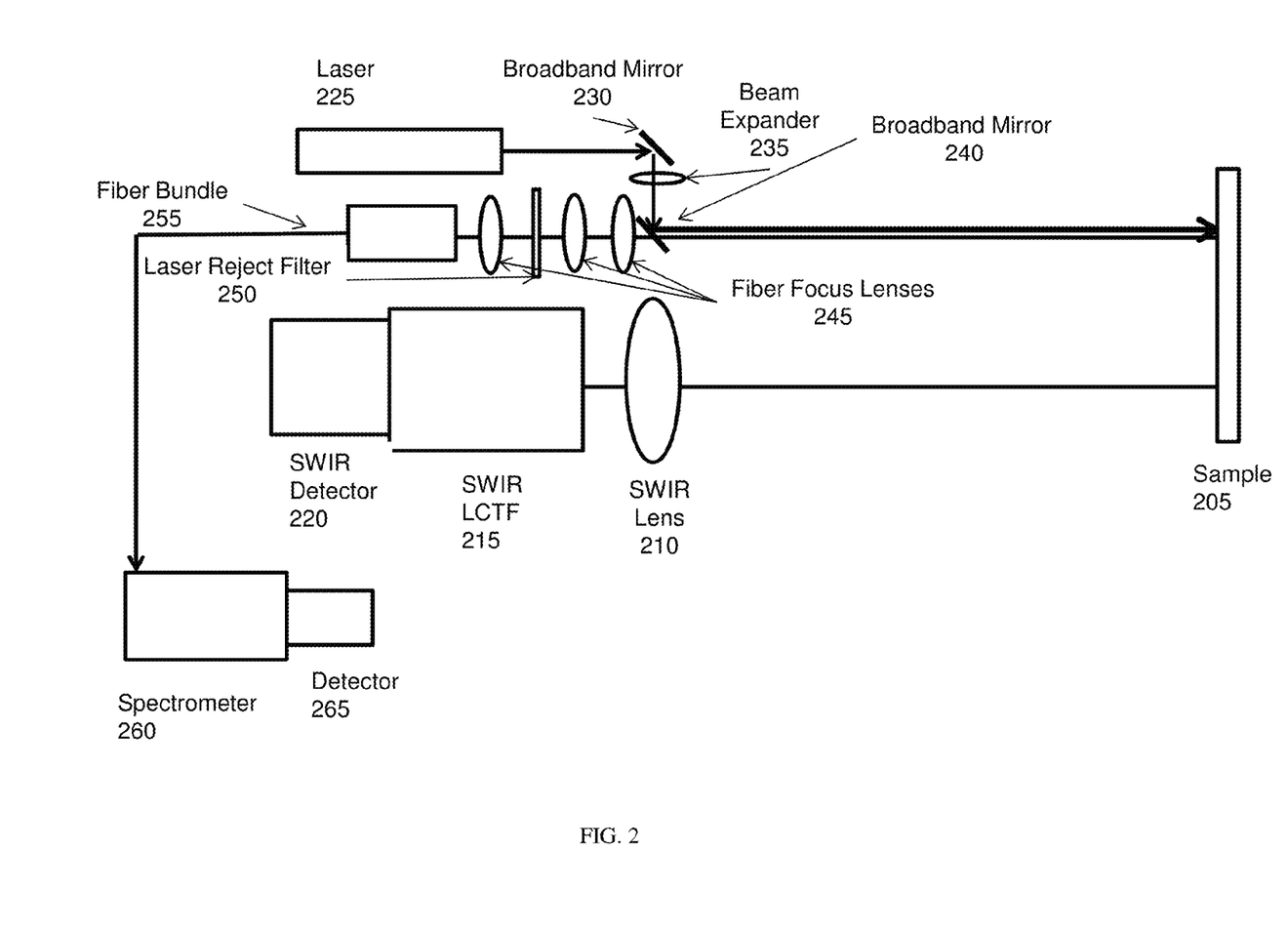
FIG. 2 is a schematic representation of a system of the present disclosure.

FIG. 2 is illustrative of another embodiment of a system of the present disclosure. A first plurality of interacted photons may be generated from the sample and may be collected using a lens 210 and directed to a filter 215a. In one embodiment, this lens 210 may comprise at least one reflective and/or refractive optic. Examples include, but are not limited to telescope optics, zoom optics, and fixed refractive lenses. In one embodiment, the filter may comprise a tunable filter configured to filter the interacted photons into a plurality of wavelength bands. The photons may be detected by a SWIR detector 220. The SWIR detector 220 may be configured to generate at least one SWIR data set. This data set may comprise at least one SWIR hyperspectral image. In another embodiment, the SWIR data set may comprise at least one of a SWIR spectrum and a spatially accurate wavelength resolved SWIR image.

A processor (not illustrated) may be configured to analyze the SWIR data set and identify a second location comprising the unknown material. The system 200 may comprise a laser 225 configured to illuminate a sample comprising an unknown material 205 to generate a second plurality of interacted photons. Laser illumination light may be directed to the sample 205 via a plurality of mechanisms including broadband mirrors 230, 240 and a beam expander 235. The second plurality of interacted photons may be passes through a plurality of fiber focus lenses 245 and a laser rejection filter 250 to FAST device 255. In one embodiment, at least one of lens 210 and lens 245 may comprise at least one reflective and/or refractive optic. Examples include, but are not limited to telescope optics, zoom optics, and fixed refractive lenses.

The FAST device 255 may be operatively coupled to the entrance slit of a spectrometer 260 configured to detect the interacted photons from the one-dimensional end of the FAST device and generate a plurality of spatially resolved Raman spectra. These spectra may be detected by the Raman detector 265 to generate at least one Raman data set representative of the second location. This Raman data set may comprise a plurality of spatially resolved Raman spectra. In another embodiment, the Raman data set may comprise at least one of: a hyperspectral Raman image and a spatially accurate wavelength resolved Raman image. A processor (not illustrated) may be configured to analyze the Raman data set.

In another embodiment, the present disclosure provides for generating SWIR hyperspectral images using dual polarization. In one embodiment, illustrated by FIG. 3A, the sample 205 may be illuminated and/or excited by a laser illumination source 225. In another embodiment, the illumination source may comprise a passive illumination source such as solar radiation. In one embodiment, it is possible to illuminate the sample from a laser directly in an oblique direction.

Figure 3A:
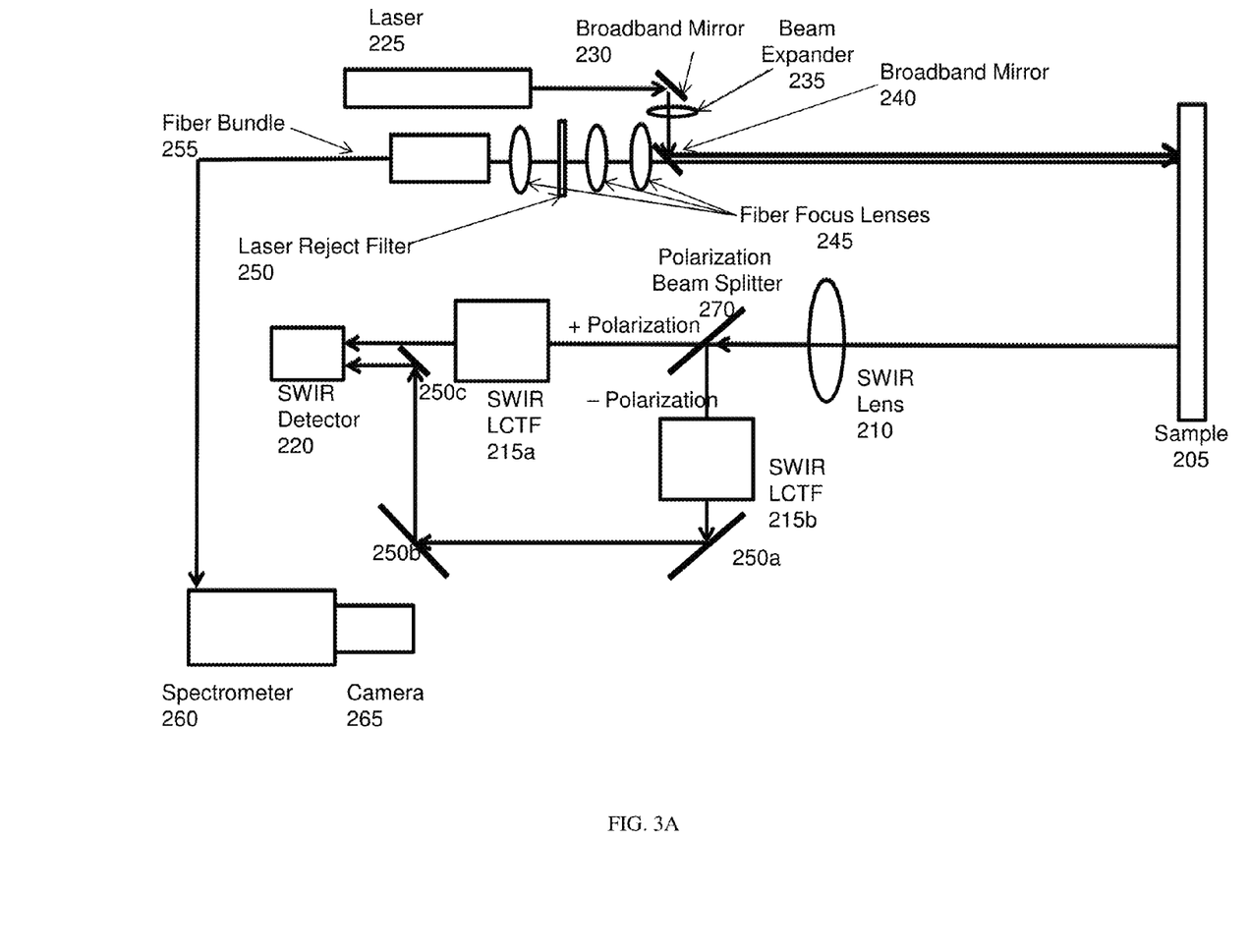
FIG. 3A is a schematic representation of a system of the present disclosure comprising dual polarization.

The embodiment of FIG. 3A comprises two independently tunable filters 215a, 215b along distinct orthogonal beam paths for the orthogonal polarization components emerging from polarization beam splitter 270. In one embodiment, the tunable filters may comprise at least one of: a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, a Fabry Perot liquid crystal tunable filter, and combinations thereof. In this arrangement, the paths of the filtered beams are not parallel through the tunable filters 215a, 215b, but are directed by appropriate reflectors (e.g., mirrors) 250a, 250b, 250c to a SWIR detector 220, at which the orthogonal components, which can be at the same or different passband wavelengths $\omega_1$ and $\omega_2$. In one embodiment, the components may be combined and directed to a detector 220 through a lens assembly. In another embodiment, the components may be kept separate as they are directed to the detector 220. However, the beam paths from one beam splitter 270 to the other 250 (via individual tunable filters 215a, 215b) may be made symmetrical to avoid, for example, need for infinitely-corrected optics. In FIG. 3A, the detector 220 may comprise other detectors including but not limited to: a CCD, a CMOS, an InGaAs, a PtSi, an InSb detector, a HgCdTe detector, and combinations thereof.

In FIG. 3A, the two tunable filters 215a, 215b may be tuned in unison to the same wavelengths ($\omega_1 = \omega_2$) using an tunable filter controller (not illustrated). It is possible to configure the controller to independently tune the passband wavelengths $\omega_1$ and $\omega_2$ of the tunable filters 215a, 215b that respectively process orthogonal components of the input. Therefore, by appropriate control, the tunable filters can be tuned to the same wavelength or to two different passband wavelengths ($\omega_1 \neq \omega_2$) at the same time. The controller may be programmable or implemented in software to allow a user to selectively tune each tunable filters 215a, 215b as desired.

Figure 3B:
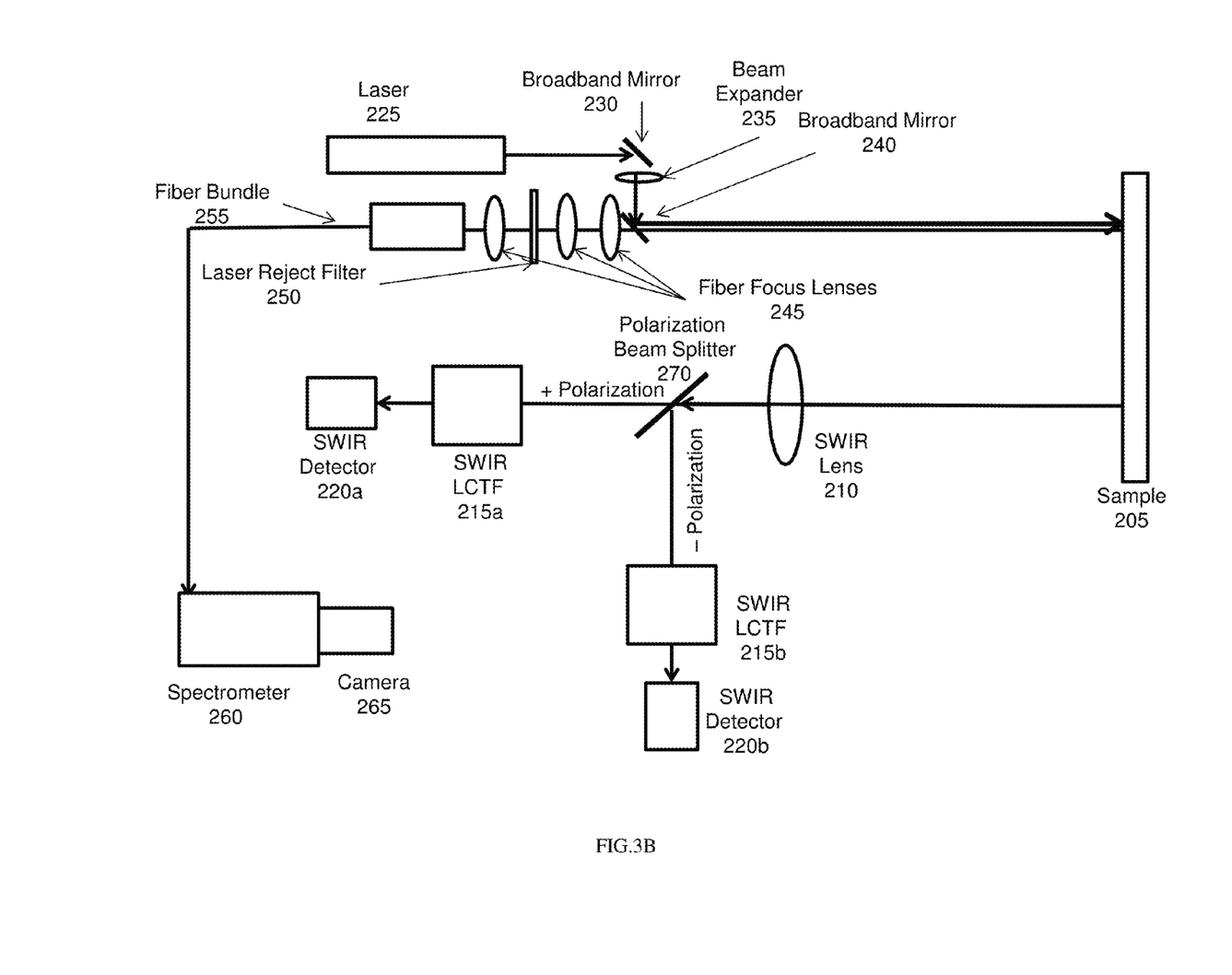
FIG. 3B is a schematic representation of a system of the present disclosure comprising dual polarization.

In the embodiment of FIG. 3A, a fast switching mechanism (not shown) may be provided to switch between the two views (or spectral images) corresponding to spectral data collected by the detector 220 from each of the tunable filters 215a, 215b. Alternatively, such two spectral views or images (from two separate LCTFs) may be combined or overlaid into a single image, for example, to increase contrast or intensity or for comparison purposes. The embodiment in FIG. 3A is shown to include a single CCD detector 220 to capture the filtered signals received from the tunable filters 215a, 215b. In another embodiment, mirror 250c may be removed and two detectors cameras may be used. An exemplary embodiment of such a configuration is illustrated in FIG. 3B. Each detector 220a and 220b may be optically coupled to a corresponding one of the two tunable filters 215a, 215b to capture filtered signals from the tunable filters and to responsively generate electronic signals that enable display of spectral images of the illuminated sample 205. The present disclosure contemplates that any number of optical filters and associated detectors may be used to achieve the benefit of dual polarization as described herein.

In one embodiment, the two filtered signals may be detected simultaneously. As discussed herein, simultaneous detection of two different wavelengths holds potential for real-time detection when displayed in a non-overlapping configuration (side-by-side, top to bottom, etc.). In another embodiment, the two filtered signals may be detected sequentially.

It is noted here that although laser light may be coherent, the light received from the sample 205 (e.g., light emitted, scattered, absorbed, and/or reflected) and fed to the tunable filters 215a, 215b may not be coherent. Therefore, wavefront errors may not be present or may be substantially avoided in the two tunable filters versions in FIGS. 3A and 3B because of processing of non-coherent light by each LCTF 215a, 215b.

Figure 4:
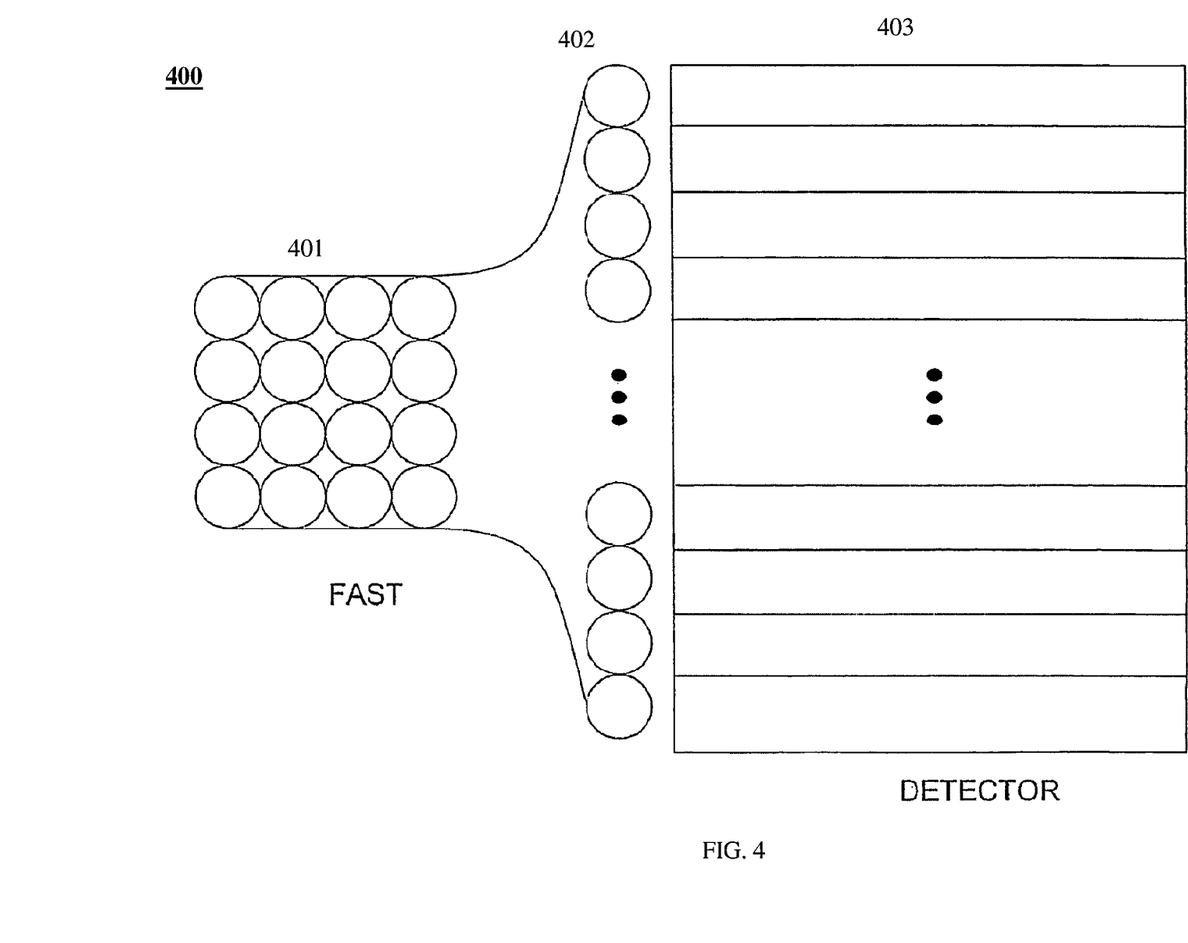
FIG. 4 is a schematic representation of a FAST device.
Figure 5:
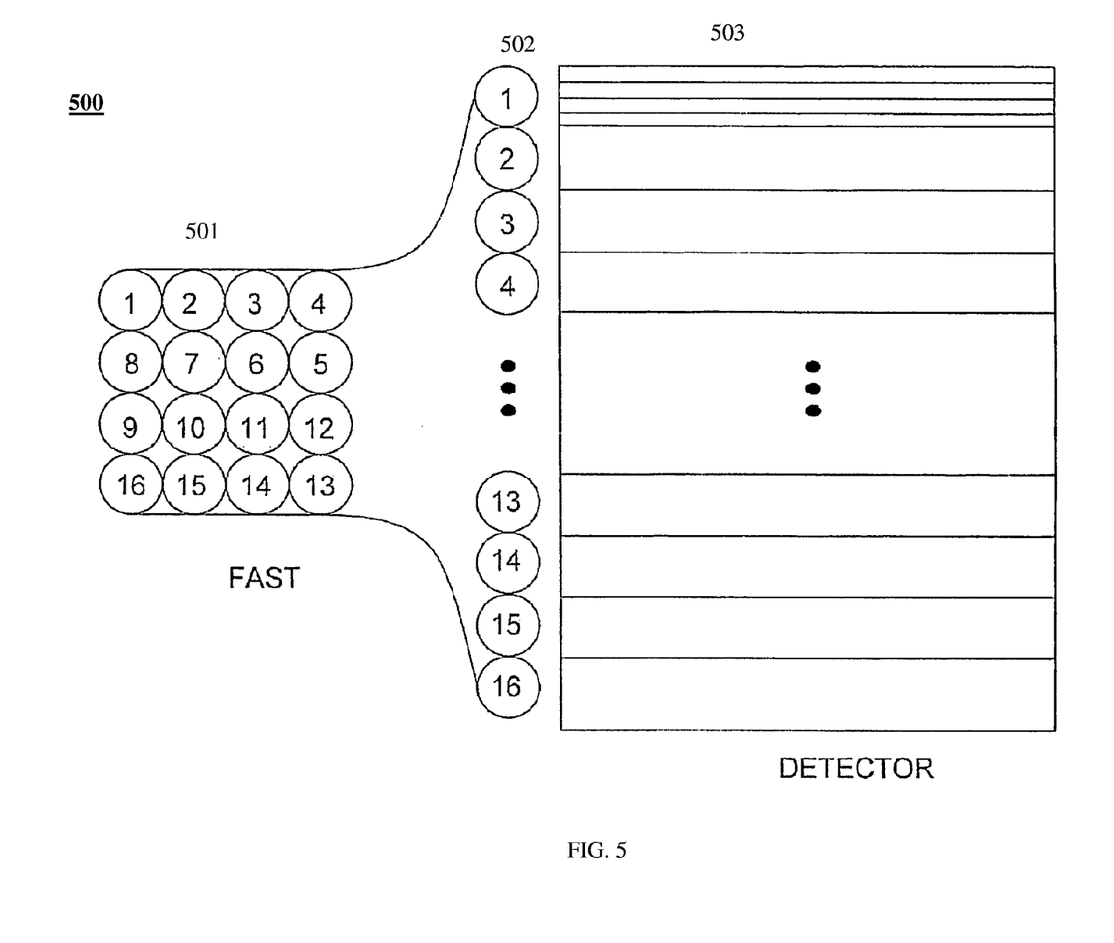
FIG. 5 is a schematic representation of a FAST device illustrating spatial knowledge of the various fibers.
Figure 6:
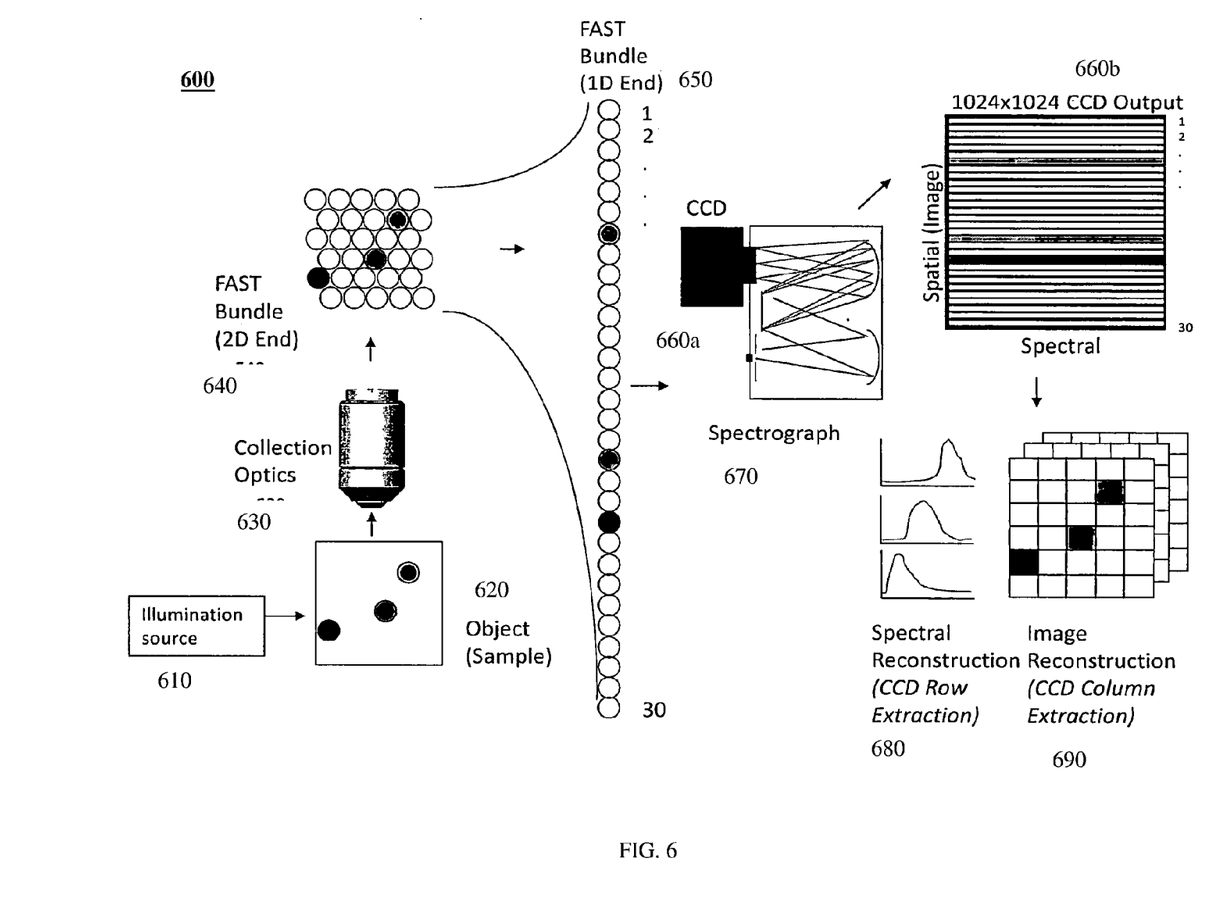
FIG. 6 is illustrative of the FAST device and its basic operation.

The FAST device is more fully described in FIGS. 4-6. The construction of the FAST array requires knowledge of the position of each fiber at both the imaging end and the distal end of the array as shown, for example, in the diagram of FIG. 4 where a total of sixteen fibers are shown numbered in correspondence between the imaging end 401 and the distal end 402 of the fiber bundle. As shown in FIG. 4, a FAST fiber bundle 400 may feed optical information from its two-dimensional non-linear imaging end 401 (which can be in any non-linear configuration, e.g., circular, square, rectangular, etc.) to its one-dimensional linear distal end 402, which feeds the optical information into associated detector rows 403. The distal end may be positioned at the input to a photon detector 403, such as a CCD, a complementary metal oxide semiconductor ("CMOS") detector, or a focal plane array sensor (such as InGaAs, InSb, metal oxide semiconductor controlled thyristor ("MCT"), etc.). Photons exiting the distal end fibers may be collected by the various detector rows. Each fiber collects light from a fixed position in the two-dimensional array (imaging end) and transmits this light onto a fixed position on the detector (through that fiber's distal end).

FIG. 5 is a schematic representation of a non-limiting exemplary spatial arrangement of fibers at the imaging end 501 and the distal end 502. Additionally, as shown in FIG. 5, each fiber of the FAST fiber bundle 500 may span more than one detector row in detector 503, allowing higher resolution than one pixel per fiber in the reconstructed image.

FIG. 6 is a schematic representation of a system comprising a traditional FAST device. The knowledge of the position of each fiber at both the imaging end and the distal end of the array and each associated spectra is illustrated in FIG. 6 by labeling these fibers, or groups of fibers) A, B, and C, and my assigning each a color.

The system 600 comprises an illumination source 610 to illuminate a sample 620 to thereby generate interacted photons. These interacted photons may comprise photons selected from the group consisting of: photons scattered by the sample, photons absorbed by the sample, photons reflected by the sample, photons emitted by the sample, and combinations thereof. These photons are then collected by collection optics 630 and received by a two-dimensional end of a FAST device 640 wherein said two-dimensional end comprises a two-dimensional array of optical fibers. The two-dimensional array of optical fibers is drawn into a one-dimensional fiber stack 650. The one-dimensional fiber stack is oriented at the entrance slit of a spectrograph 670. As can be seen from the schematic, the one-dimensional end 650 of a traditional FAST device comprises only one column of fibers. The spectrograph 670 may function to separate the plurality of photons into a plurality of wavelengths. The photons may be detected at a detector 660*a* to thereby obtain a spectroscopic data set representative of said sample. 660*b* is illustrative of the detector output, 680 is illustrative of spectral reconstruction, and 690 is illustrative of image reconstruction.

With the detection FAST array aligned to the hyperspectral FOV, Raman interrogation of the areas determined from the hyperspectral data can be done through the ALS process: moving the laser spot to those areas and collecting the FAST spectral data set. A false-color (or "pseudo color") overlay may be applied to images.

In another embodiment, the FAST device may be configured to provide for spatially and spectrally parallelized system. Such embodiment is more fully described in U.S. patent Ser. No. 12/759,082, filed on Apr. 13, 2010, entitled "Spatially and Spectrally Parallelized Fiber Array Spectral Translator System and Method of Use", which is hereby incorporated by reference in its entirety. Such techniques hold potential for enabling expansion of the number of fibers, which may improve image fidelity, and/or scanning area.

The present disclosure also provides for a method for analyzing a sample comprising an unknown material. The method may comprise first scanning a location using SWIR hyperspectral imaging and then targeting a second location for further analysis and/or confirmation of the presence of a particular material using Raman spectroscopy.

Figure 7:
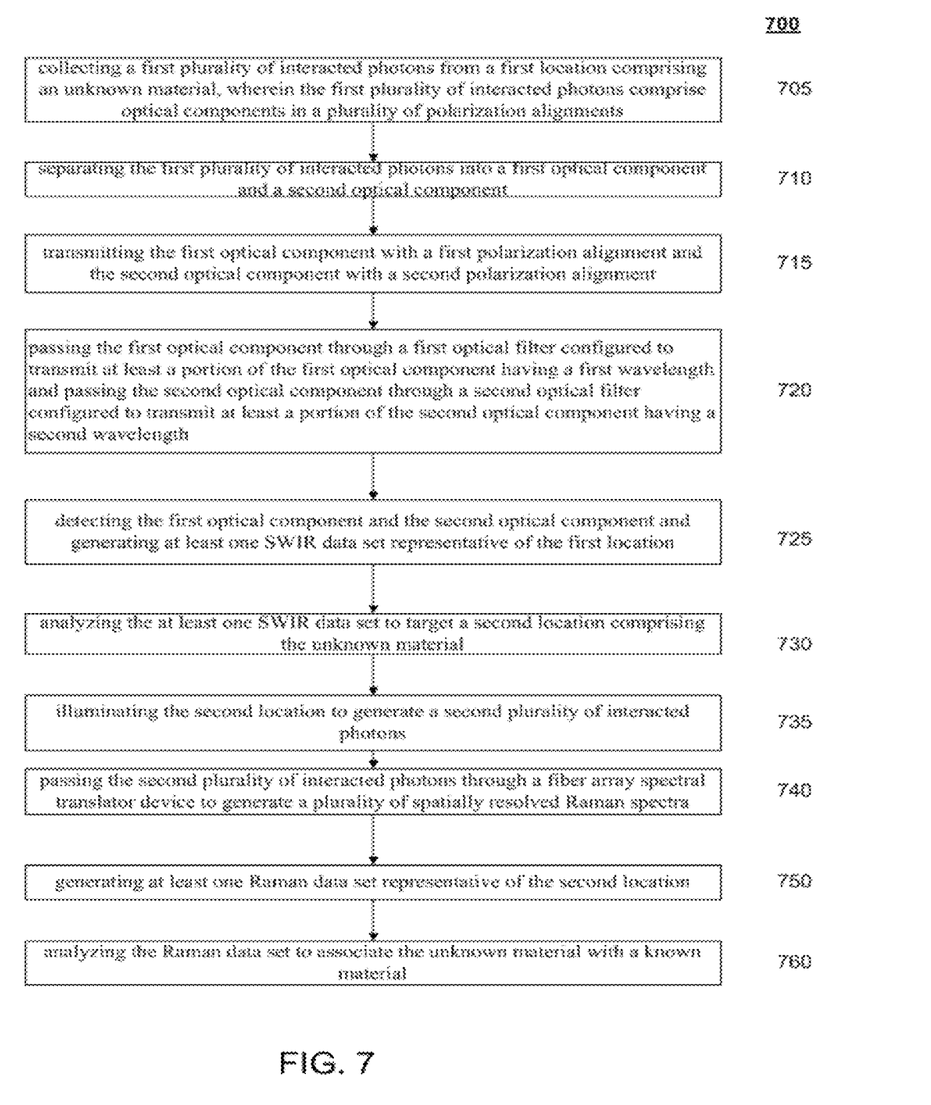
FIG. 7 is illustrative of a method of the present disclosure.

In one embodiment, illustrated by FIG. 7, the method 700 may comprise collecting a plurality of interacted photons from a first location comprising an unknown material in step 705. These interacted photons may comprise optical components in a plurality of polarization alignments. In step 710, the first plurality of interacted photons may be separated into a first optical component and a second optical component. In step 715, the first optical component may be transmitted with a first polarization alignment and the second optical component may be transmitted with a second polarization alignment. In step 720, the first optical component may be passed through a first optical filter configured to transmit at least a portion of the first optical component having a first wavelength. In step 725, the second optical component may be passed through a second optical filter configured to transmit at least a portion of the second optical component having a second wavelength.

The first optical component and the second optical component may be detected in step 730 to generate at least one SWIR data set representative of the first location. In one embodiment, a first SWIR data set can be generated using the first optical component and a second SWIR data set can be generated using the second optical component. The SWIR data set(s) may be analyzed in step 735 to target a second location comprising the unknown material.

The second location may be illuminated in step 740 to generate a second plurality of interacted photons. The second plurality of interacted photons may be passed through a FAST device in step 745 and at least one Raman data set generated in step 750. This Raman data set may be analyzed in step 755 to associated the unknown material with a known material.

In addition to the systems and methods contemplated by the present disclosure, software may hold potential for collecting, processing and displaying hyperspectral and chemical. Such software may comprise ChemImage Xpert® available from ChemImage Corporation, Pittsburgh, Pa.

In one embodiment, the method may further provide for applying a fusion algorithm to the test data set and the Raman data set. In one embodiment, a chemometric technique may be applied to a data set wherein the data set comprises a multiple frame image. This results in a single frame image wherein each pixel has an associated score (referred to as a "scored image"). This score may comprise a probability value indicative of the probability the material at the given pixel comprises a specific material (i.e., a chemical, biological, explosive, hazardous, or drug material). In one embodiment, a scored image may be obtained for both the test data set and the Raman data set. Bayesian fusion, multiplication, or another technique may be applied to these sets of scores to generate a fused score value. This fusion holds potential for increasing confidence in a result and reducing the rate of false positives. In one embodiment, this fused score value may be compared to a predetermined threshold or range of thresholds to generate a result. In another embodiment, weighting factors may be applied so that more reliable modalities are given more weight than less reliable modalities.

In one embodiment, the method may further provide for "registration" of images generated using different modalities. Such registration addresses the different image resolutions of different spectroscopic modalities which may result in differing pixel scales between the images of different modalities. Therefore, if the spatial resolution in an image from a first modality is not equal to the spatial resolution in the image from the second modality, portions of the image may be extracted out. For example, if the spatial resolution of a SWIR image does not equal the spatial resolution of a Raman image, the portion of the SWIR image corresponding to the dimensions of the Raman image may be extracted and this portion of the SWIR image may then be multiplied by the Raman image.

Figure 8:
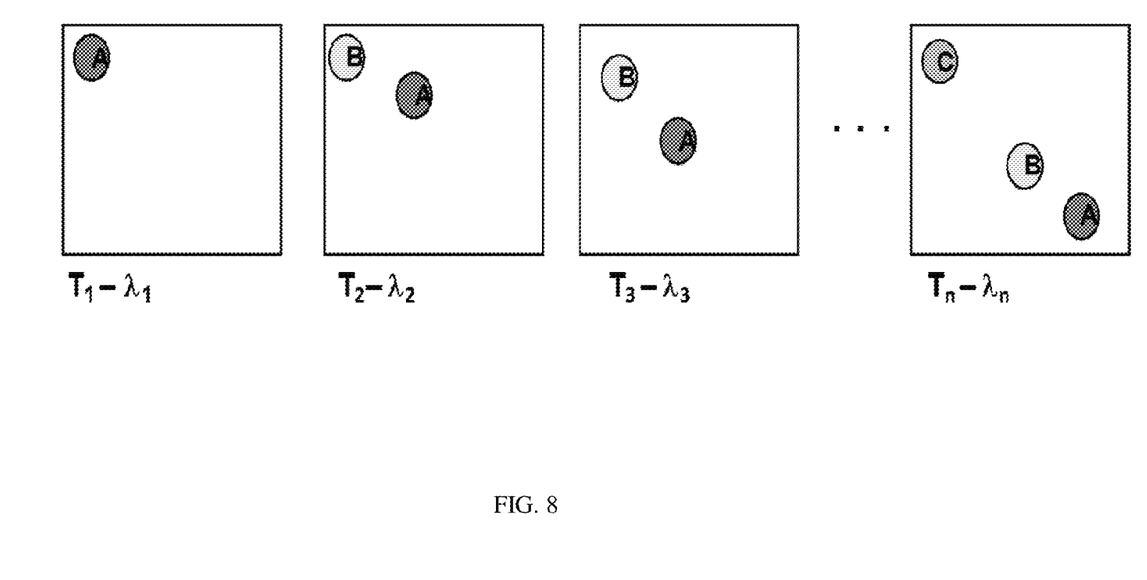
FIG. 8 is illustrative of a target-tracking algorithm of the present disclosure.

In one embodiment, the method may further comprise application of algorithms for at least one of: sensor fusion, data analysis, and target-tracking. One embodiment of a target tracking algorithm is illustrated in FIG. 8. The schematic illustrates a technique that may be implemented for dynamical chemical imaging in which more than one object of interest passes continuously through the FOV. Such continuous stream of objects results in the average amount of time required to collect all frames for a given object being equivalent to the amount of time required to capture one frame as the total number of frames under collection approaches infinity (frame collection rate reaches a steady state). In other words, the system is continually collecting the frames of data for multiple objects simultaneously and with every new frame, the set of frames for any single object is completed. In one embodiment, the objects of interest are of a size substantially smaller than the FOV to allow more than one object to be in the FOV at any given time.

Referring again to FIG. 8, Object A is present in a slightly translated position in every frame. Each frame is collected at a different wavelength. Tracking of Object A across all frames allows the spectrum to be generated for every pixel in Object A. The same process is followed for Object B and Object C. A continual stream of objects can be imaged with the wavelengths being captured for every time, $t_i$, is updated in a continuous loop.

Although the disclosure is described using illustrative embodiments provided herein, it should be understood that the principles of the disclosure are not limited thereto and may include modification thereto and permutations thereof.

What is claimed is:

1. A system comprising:
   a first subsystem comprising:
      a first collection optics configured to collect a first plurality of interacted photons having optical components in a plurality of polarization alignments from a first location comprising an unknown material;
      a polarization assembly configured to receive the first plurality of interacted photons and separate the first plurality of interacted photons into a first optical component with a first polarization alignment and a second optical component with a second polarization alignment;
      a first optical filter configured to receive at least a portion of the first optical component and generate a first filtered component having a first wavelength;
      a second optical filter configured to receive at least a portion of the second optical component and generate a second filtered component having a second wavelength; and
      at least one SWIR detector configured to detect one or more of the first filtered component and the second filtered component and generate at least one SWIR data set; and
   a second subsystem comprising:
      an illumination source configured to illuminate a second location comprising the unknown material and generate a second plurality of interacted photons,
      a second collection optics configured to collect the second plurality of interacted photons;
      a fiber array spectral translator device having a two-dimensional array of optical fibers drawn into a one-dimensional fiber stack, wherein the fiber array spectral translator device is configured to convert a two-dimensional field of view into a curvilinear field of view;
      a spectrometer comprising an entrance slit coupled to the one-dimensional end of the fiber stack to generate a plurality of spatially resolved Raman spectra; and
      a Raman detector coupled to the spectrometer to detect the spatially resolved Raman spectra and generate at least one Raman data set.

2. The system of claim 1, wherein at least one of the first collection optics and the second collection optics further comprises a telescope optic.

3. The system of claim 1, wherein at least one of the first optical filter and the second optical filter further comprises a tunable filter.

4. The system of claim 3, wherein the tunable filter is selected from the group consisting of a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, and a Fabry Perot liquid crystal tunable filter.

5. The system of claim 1, wherein the at least one SWIR detector comprises a first SWIR detector configured to detect the first filtered component, and a second SWIR detector configured to detect the second filtered component.

6. The system of claim 1, wherein the at least one SWIR detector further comprises a focal plane array.

7. The system of claim 6, wherein the focal plane array further comprises one or more of an InGaAs detector, a CMOS detector, an InSb detector, an MCT detector, an ICCD detector, and a CCD detector.

8. The system of claim 1, wherein the Raman detector further comprises a focal plane array.

9. The system of claim 8, wherein the focal plane array further comprises one or more of an InGaAs detector, a CMOS detector, an InSb detector, an MCT detector, an ICCD detector, and a CCD detector.

10. The system of claim 1 further comprising at least one reference database comprising at least one reference data set associated with a known material.

11. The system of claim 1 further comprising a processor configured to analyze one or more of the at least one SWIR data set and the at least one Raman data set.

12. A method comprising:
   collecting a first plurality of interacted photons having optical components in a plurality of polarization alignments from a first location comprising an unknown material;
   separating the first plurality of interacted photons into a first optical component having a first polarization alignment and a second optical component having a second polarization alignment;
   passing at least a portion of the first optical component through a first optical filter configured to generate a first filtered component having a first wavelength;
   passing at least a portion of the second optical component through a second optical filter configured to generate a second filtered component having a second wavelength;
   detecting the first filtered component and the second filtered component to generate at least one SWIR data set;
   analyzing the at least one SWIR data set to target a second location comprising the unknown material;
   illuminating the second location to generate a second plurality of interacted photons;
   passing the second plurality of interacted photons through a fiber array spectral translator device to generate a plurality of spatially resolved Raman spectra;
   generating at least one Raman data set of the spatially resolved Raman spectra; and
   analyzing the Raman data set to associate the unknown material with a known material.

13. The method of claim 12, wherein the first filtered component is detected by a first SWIR detector and the second filtered component is detected by a second SWIR detector.

14. The method of claim 12, wherein the first filtered component and the second filtered component are detected using one SWIR detector.

15. The method of claim 14, wherein the first filtered component and the second filtered component are overlaid.

16. The method of claim 14, wherein the first filtered component and the second filtered component are not overlaid.

17. The method of claim 12, wherein one or more of the at least one SWIR data set and the at least one Raman data set are analyzed by comparison with at least one reference data set, associated with a known material.

18. The method of claim 17, wherein the comparison is achieved by applying at least one chemometric technique.

19. The method of claim 12, wherein at least a portion of the first location and at least a portion of the second location overlap.

20. The method of claim 12, wherein the second location is located within the first location.

21. The method of claim 12, wherein the at least one SWIR data set further comprises one or more of a SWIR spectrum and a spatially accurate wavelength resolved SWIR image.

22. The method of claim 12, wherein the at least one SWIR data set further comprises at least one hyperspectral SWIR image.

\* \* \* \* \*